(12) United States Patent
Carson et al.

(10) Patent No.: US 8,357,715 B2
(45) Date of Patent: Jan. 22, 2013

(54) HETERO-SUBSTITUTED ACETANILIDE DERIVATIVES AS ANALGESIC AGENTS

(75) Inventors: John R. Carson, Norristown, PA (US); James J. McNally, Souderton, PA (US)

(73) Assignee: Janssen Pharmaceutica, NV, Beerse (BE)

( * ) Notice: Subject to any disclaimer, the term of this patent is extended or adjusted under 35 U.S.C. 154(b) by 401 days.

(21) Appl. No.: 12/751,382

(22) Filed: Mar. 31, 2010

(65) Prior Publication Data

US 2010/0204284 A1    Aug. 12, 2010

Related U.S. Application Data

(62) Division of application No. 10/778,980, filed on Feb. 13, 2004, now Pat. No. 7,718,692.

(60) Provisional application No. 60/439,761, filed on Jan. 13, 2003.

(51) Int. Cl.
*A61K 31/415* (2006.01)
(52) U.S. Cl. ..................................... 514/406; 514/396
(58) Field of Classification Search .................. 514/406, 514/396
See application file for complete search history.

(56) References Cited

U.S. PATENT DOCUMENTS

| | | | |
|---|---|---|---|
| 2,799,679 | A | 7/1957 | Ekenstam et al. |
| 3,689,555 | A | 9/1972 | Schut |
| 4,329,366 | A | 5/1982 | Nashed et al. |
| 4,532,249 | A | 7/1985 | Molnar et al. |
| 4,904,672 | A | 2/1990 | Baker et al. |
| 5,554,636 | A | 9/1996 | Bazan et al. |

FOREIGN PATENT DOCUMENTS

| | | |
|---|---|---|
| DE | 3534765 A1 | 4/1987 |
| JP | 57007431 A | 1/1982 |
| JP | 04041425 A | 2/1992 |
| WO | WO 96/32100 A1 | 10/1996 |
| WO | WO 97/33860 A1 | 9/1997 |

OTHER PUBLICATIONS

PCT International Search Report dated Aug. 25, 2004 for PCT Application No. PCT/IB2004/001032 which relates to U.S. Appl. No. 10/778,980.
Massey, T.E. et al., "Acetaminophen—Induced Hypothermia in Mice: Evidence for a Central Action of the Parent Compound." *Toxicology*, 1982, pp. 187-200, vol. 25.
Piletta, P. et al., "Central analgesic effect of acetaminophen but not of aspirin." *Clin. Pharm. Ther.*, 1991, pp. 350-354, vol. 49, No. 4.
Bjorkman, R. et al., "Acetaminophen blocks spinal hyperalgesia induced by NMDA and substance P." *Pain*. 1994, pp. 259-264, vol. 57.
Srikiatkhachorn, A., "Acetarninophen-induced antinociception via central 5-HT$_{2A}$ receptors." *Neurochem. Intl.*, 1999, pp. 491-498, vol. 34.
Chandrasekharan, N. V. et al., "COX-3, a cyclooxygenase-1 variant inhibited by acetaminophen and other analgesic/antipyretic drugs: Cloning, structure, and expression." *PNAS*, 2002, pp. 13926-13931, vol. 99, No. 21.
Derwent Abstract, Derwent-Acc-No. 1992-108724, JP 04041425.
Wikipedia "Local Anesthetic" HTTP://EN.WIKIPEDIA.ORG/WIKI/LOCAL_ANESTHETIC.

*Primary Examiner* — Shengjun Wang

(57) ABSTRACT

Hetero-substituted acetanilide derivatives are disclosed as analgesic agents. The compounds of the invention are useful in methods for treating a disease or condition in a mammal characterized by pain and/or fever.

4 Claims, No Drawings

HETERO-SUBSTITUTED ACETANILIDE DERIVATIVES AS ANALGESIC AGENTS

CROSS REFERENCE TO RELATED APPLICATIONS

This Application is a divisional of application Ser. No. 10/778,980 filed Feb. 13, 2004, now U.S. Pat. No. 7,718,692, which claims priority to U.S. Provisional Patent Application No. 60/439,761, filed Jan. 13, 2003, now abandoned, which are hereby incorporated by reference in their entirety.

STATEMENT REGARDING FEDERALLY SPONSORED RESEARCH OR DEVELOPMENT

The research and development of the invention described below was not federally sponsored.

BACKGROUND OF THE INVENTION

Para-aminophenol type nonnarcotic analgesics/antipyretics have been known for over a century. They act to decrease fever by an effect on the hypothalamus leading to sweating and vasodilation and inhibit the effect of pyrogens on the hypothalamic heat-regulating centers. The mechanism of the analgesic action of these agents is not fully understood. Although this analgesic action was initially thought to be peripherally mediated, current evidence supports a central mode of action (Acetaminophen-induced hypothermia in mice: evidence for a central action of the parent compound. Massey, Thomas E.; Walker, Robin M.; McElligott, Timothy F.; Racz, William J. Dep. Pharmacol. Toxicol., Queen's Univ., Kingston, ON, Can. Toxicology (1982), 25(2-3), 187-200; Central analgesic effect of acetaminophen but not of aspirin. Piletta, Pierre; Porchet, Herve C.; Dayer, Pierre. Dep. Med., Univ. Hosp., Geneva, Switz. Clin. Pharmacol. Ther. (St. Louis) (1991), 49(4), 350-4.; Acetaminophen blocks spinal hyperalgesia induced by NMDA and substance P. Bjoerkman, R.; Hallman, K. M.; Hedner, J.; Hedner, T.; Henning, M. Pain (1994), 57(3), 259-64.). Suggested biochemistries for this central mode of action include interaction with the L-arginine-NO pathway (Piletta, ibid), modulation of brain serotonin receptor level (Acetaminophen-induced antinociception via central 5-HT2A receptors. Srikiatkhachorn, Anan; Tarasub, Naovarut; Govitrapong, Piyarat. Neurochem. Int. (1999), 34(6), 491-498.) or inhibition of COX-3 enzyme activity (N. V. Chandrasekharan, Hu Dai, K. Lamar Turepu Roos, Nathan K. Evanson, Joshua Tomsik, Terry S. Elton, and Daniel L. Simmons (2002) COX-3, a cyclooxygenase-1 variant inhibited by acetaminophen and other analgesic/antipyretic drugs: Cloning, structure, and expression. Proc. Natl. Acad. Sci. USA, 99:13926-13931, 2002). Inhibition of the COX-3 enzyme, recently cloned from brain, points to the possible inhibition by these agents of CNS prostaglandin synthesis. The antipyretic and analgesic effects of these compounds are comparable to those of aspirin.

Para-aminophenol type nonnarcotic analgesics have been used to control pain due to headache, earache, dysmenorrhea, arthralgia, myalgia, musculoskeletal pain, arthritis, immunizations, teething, tonsillectomy. They are also used to reduce fever in bacterial or viral infections and as a substitute for aspirin in upper GI disease, aspirin allergy, bleeding disorders, clients on anticoagulant therapy, and gouty arthritis.

Unexamined Japanese patent application 57007431(Jan. 14, 1982) discloses various analgesic phenols. This application, however, does not disclose or suggest the compounds of the present invention.

U.S. Pat. No. 4,532,249 discloses derivatives of para-acylaminophenol having analgesic activity. This patent, however, does not disclose or suggest the compounds of the present invention.

U.S. Pat. No. 3,689,555 discloses norbornyl aminoacetanilides for uses in analgesics. This patent, however, does not disclose or suggest the compounds of the present invention.

International Patent Applications WO 96/32100 and WO 97/33860 disclose aminoalkyl-acetamides as analgesic agents. These applications, however, do not disclose or suggest the compounds of the present invention.

U.S. Pat. No. 5,554,636 discloses cyclicsulfonamidylalkylacetamides as analgesic agents. This patent, however, does not disclose or suggest the compounds of the present invention.

In view of their lack of ulcerative and anticoagulation effects, para-aminophenol type nonnarcotic analgesics fill a need in analgesic and antipyretic therapies in patients with problems related to GI and cardiovascular disorders, and there is thus a continuing need for new pharmaceutical compounds of this class.

SUMMARY OF THE INVENTION

The present invention is directed to analgesic and antipyretic uses of compositions comprising a compound of Formula (I):

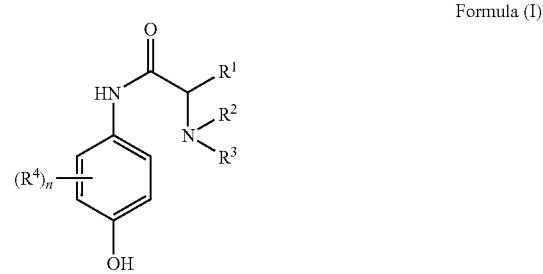

Formula (I)

wherein:
$R^1$ and $R^2$ taken together with the atoms to which they are attached form a radical selected from the group consisting of a 5 to 10 membered cycloheteroalkanyl, 5 to 10 membered cycloheteroalkenyl and a 5 to 10 membered heteroaryl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;
$R^3$ is hydrogen or $C_{1-6}$alkanyl;
$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;
n is an integer from 1 to 3;
and enantiomers, diastereomers, tautomers, solvates, or pharmaceutical acceptable salts thereof.

The present invention is directed to analgesic and antipyretic uses of compositions comprising a compound of Formula (II):

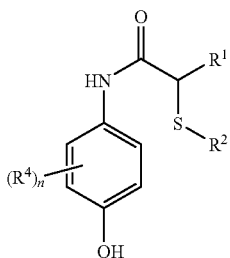

Formula (II)

wherein:
R$^1$ is a substituent independently selected from the group consisting of hydrogen and C$_{1-6}$alkanyl;
R$^2$ is a substituent independently selected from the group consisting of hydrogen, C$_{1-6}$alkanyl and dioxo;
or R$^1$ and R$^2$ taken together with the atoms to which they are attached form a radical selected from the group consisting of a 5 to 10 membered cycloheteroalkanyl, 5 to 10 membered cycloheteroalkenyl and a 5 to 10 membered heteroaryl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of C$_{1-6}$alkanyl and oxo;
R$^4$ is a substituent selected from the group consisting of hydrogen, C$_{1-6}$alkanyl, C$_{1-6}$alkanyloxy, fluorinated alkanyl, fluorinated alkanyloxy, halogen, hydroxyl, nitro, amino, C$_{1-6}$alkanylamino; C$_{1-6}$dialkanylamino and cyano;
n is an integer from 1 to 3;
and enantiomers, diastereomers, tautomers, solvates, or pharmaceutically acceptable salts thereof.

Finally, the present invention is directed to pharmaceutical compositions containing compounds of Formula (I) wherein R$^3$ is hydrogen and R$^1$ and R$^2$ taken together form an optionally substituted pyrrole.

DETAILED DESCRIPTION OF THE INVENTION

As used herein, the following underlined terms are intended to have the following meanings:

"C$_{a-b}$" (where a and b are integers) refers to a radical containing from a to b carbon atoms inclusive. For example, C$_{1-3}$ denotes a radical containing 1, 2 or 3 carbon atoms "Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl( ), prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are (C$_1$-C$_6$)alkyl, with (C$_1$-C$_3$) being particularly preferred.

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are (C$_{1-8}$)alkanyl, with (C$_{1-3}$) being particularly preferred.

"Alkenyl" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkenyl" refers to an unsaturated branched, straight-chain or cyclic monovalent hydrocarbon radical having at least one carbon carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Heteroalkyl" and Heteroalkanyl" refer to alkyl or alkanyl radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkanyl radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimmino (—NR'—NR'—), azino (=N—N=), azo (—N=N—), azoxy (—N—O—N—), azimino (—NR'—N=N—), phosphano (—PH—), λ$^4$-sulfano (—H$_2$—), sulfonyl (—S(O)$_2$—), and the like, where each R' is independently hydrogen or (C$_1$-C$_6$)alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is $(C_{5-20})$ aryl, with $(C_{5-10})$ being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. [In preferred embodiments, the arylalkyl group is $(C_{6-26})$ arylalkyl, e.g., the alkanyl, alkenyl or alkynyl moiety of the arylalkyl group is $(C_{1-6})$ and the aryl moiety is $(C_{5-20})$. In particularly preferred embodiments the arylalkyl group is $(C_{6-13})$, e.g., the alkanyl, alkenyl or alkynyl moiety of the arylalkyl group is $(C_{1-3})$ and the aryl moiety is $(C_{5-10})$. Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyl; ethanyloxy; propanyloxy groups such as propan-1-yloxy $(CH_3CH_2CH_2O—)$, propan-2-yloxy $((CH_3)_2CHO—)$, cyclopropan-1-yloxy, etc.; butanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are $(C_{1-8})$ alkanyloxy groups, with $(C_{1-3})$ being particularly preferred.

"Parent Heteroaromatic Ring System:" refers to a parent aromatic ring system in which one carbon atom is replaced with a heteroatom. Heteratoms to replace the carbon atoms include N, O, and S. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred.

"Cycloheteroalkyl:" refers to a saturated or unsaturated monocyclic or bicyclic alkyl radical in which one carbon atom is replaced with N, O or S. In certain specified embodiments the cycloheteroalkyl may contain up to four heteroatoms independently selected from N, O or S. Typical cycloheteroalkyl moieties include, but are not limited to, radicals derived from imidazolidine, morpholine, piperazine, piperidine, pyrazolidine, pyrrolidine, quinuclidine, and the like. In preferred embodiments, the cycloheteroalkyl is a 3-6 membered cycloheteroalkyl.

"Cycloheteroalkanyl:" refers to a saturated monocyclic or bicyclic alkanyl radical in which one carbon atom is replaced with N, O or S. In certain specified embodiments the cycloheteroalkanyl may contain up to four heteroatoms independently selected from N, O or S. Typical cycloheteroalkanyl moieties include, but are not limited to, radicals derived from imidazolidine, morpholine, piperazine, piperidine, pyrazolidine, pyrrolidine, quinuclidine, and the like. In preferred embodiments, the cycloheteroalkanyl is a 3-6 membered cycloheteroalkanyl.

"Cycloheteroalkenyl:" refers to a saturated monocyclic or bicyclic alkenyl radical in which one carbon atom is replaced with N, O or S. In certain specified embodiments the cycloheteroalkenyl may contain up to four heteroatoms independently selected from N, O or S. Typical cycloheteroalkenyl moieties include, but are not limited to, radicals derived from imidazoline, pyrazoline, pyrroline, indoline, pyran, and the like. In preferred embodiments, the cycloheteroalkanyl is a 3-6 membered cycloheteroalkanyl.

"Substituted:" refers to a radical in which one or more hydrogen atoms are each independently replaced with the same or different substituent(s). Typical substituents include, but are not limited to, —X, —R, —O$^-$, =O, —OR, —O—OR, —SR, —S$^-$, =S, —NRR, =NR, —CX$_3$, —CN, —OCN, —SCN, —NCO, —NCS, —NO, —NO$_2$, =N$_2$, —N$_3$, —NHOH, —S(O)$_2$O$^-$, —S(O)$_2$OH, —S(O)$_2$R, —P(O)(O$^-$)$_2$, —P(O)(OH)$_2$, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, $C_{1-8}$alkyl, $C_{1-8}$alkanyloxy, fluorinated alkanyloxy, fluorinated alkyl, $C_{1-8}$alkylthio, $C_{3-8}$cycloalkyl, $C_{3-8}$cycloalkanyloxy, nitro, amino, $C_{1-8}$alkylamino, $C_{1-8}$dialkylamino, $C_{3-8}$cycloalkylamino, cyano, carboxy, $C_{1-7}$alkanyloxycarbonyl, $C_{1-7}$alkylcarbonyloxy, formyl, carbamoyl, phenyl, aroyl, carbamoyl, amidino, $(C_{1-8}$alkylamino)carbonyl, (arylamino)carbonyl and aryl$(C_{1-8}$alkyl)carbonyl.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenyl$C_{1-6}$alkanylaminocarbonyl$C_{1-6}$alkyl" substituent refers to a group of the formula

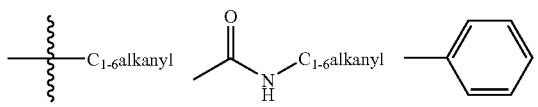

The present invention is directed to analgesic and anti-pyretic uses of compositions comprising a compound of Formula (I):

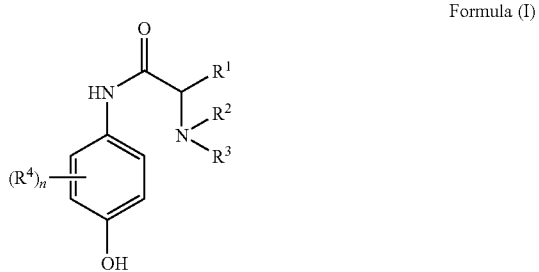

Formula (I)

wherein:
$R^1$ and $R^2$ taken together with the atoms to which they are attached form a radical selected from the group consisting of a 5 to 10 membered cycloheteroalkanyl, 5 to 10 membered cycloheteroalkenyl and a 5 to 10 membered heteroaryl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;
$R^3$ is hydrogen or $C_{1-6}$alkanyl;
$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;
n is an integer from 1 to 3;
and enantiomers, diastereomers, tautomers, solvates, or pharmaceutically acceptable salts thereof.

Embodiments of the present invention include those wherein for compounds of formula (I):
a) $R^1$ and $R^2$ taken together with the atoms to which they are attached form a 5 to 10 membered cycloheteroalkanyl radical, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;
b) $R^1$ and $R^2$ taken together with the atoms to which they are attached form a 5 to 10 membered cycloheteroalkenyl radical, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;
c) $R^1$ and $R^2$ taken together with the atoms to which they are attached form a 5 to 10 membered heteroaryl radical, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;
d) $R^1$ and $R^2$ taken together with the atoms to which they are attached form a radical selected from the group consisting of a 5 to 10 membered cycli heteroalkyl and a 5 to 10 membered heteroaryl; additionally, said radical may be further optionally substituted with one to three substituents independently selected from the group consisting of $C_{1-6}$alkanyl and oxo;
e) $R^3$ is hydrogen;
f) $R^4$ is hydrogen;
g) n is 1; and
h) combinations of a) through g) above.

Thus, exemplary embodiments of the present invention are as described below.

An embodiment of the present invention is directed to analgesic and anti-pyretic uses of compositions comprising a compound of Formula (I) wherein:
$R^1$ and $R^2$ taken together with the atoms to which they are attached form a 5 to 10 membered cycloheteroalkanyl radical, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;
$R^3$ is hydrogen or $C_{1-6}$alkanyl;
$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;
n is an integer from 1 to 3;
and enantiomers, diastereomers, tautomers, solvates, or pharmaceutically acceptable salts thereof.

Another embodiment of the present invention is directed to analgesic and anti-pyretic uses of compositions comprising a compound of Formula (I) wherein:
$R^1$ and $R^2$ taken together with the atoms to which they are attached form a 5 to 10 membered cycloheteroalkenyl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;
$R^3$ is hydrogen or $C_{1-6}$alkanyl;
$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;
n is an integer from 1 to 3;
and enantiomers, diastereomers, tautomers, solvates, or pharmaceutically acceptable salts thereof.

Still another embodiment of the present invention is directed to analgesic and anti-pyretic uses of compositions comprising a compound of Formula (I) wherein:
$R^1$ and $R^2$ taken together with the atoms to which they are attached form a 5 to 10 membered heteroaryl radical, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

$R^3$ is hydrogen or $C_{1-6}$alkanyl;

$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;

n is an integer from 1 to 3;

and enantiomers, diastereomers, tautomers, solvates, or pharmaceutically acceptable salts thereof.

Still another embodiment of the present invention is directed to analgesic and anti-pyretic uses of compositions comprising a compound of Formula (I) wherein:

$R^1$ and $R^2$ taken together with the atoms to which they are attached form a radical selected from the group consisting of a 5 to 10 membered cycloheteroalkanyl, 5 to 10 membered cycloheteroalkenyl and a 5 to 10 membered heteroaryl; additionally, said radical may be further optionally substituted with one to three substituents independently selected from the group consisting of $C_{1-6}$alkanyl and oxo;

$R^3$ is hydrogen or $C_{1-6}$alkanyl;

$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;

n is an integer from 1 to 3;

and enantiomers, diastereomers, tautomers, solvates, or pharmaceutically acceptable salts thereof.

Still yet another embodiment of the present invention is directed to analgesic and anti-pyretic uses of compositions comprising a compound of Formula (I) wherein:

$R^1$ and $R^2$ taken together with the atoms to which they are attached form a radical selected from the group consisting of a 5 to 10 membered cycloheteroalkanyl, 5 to 10 membered cycloheteroalkenyl and a 5 to 10 membered heteroaryl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

$R^3$ is hydrogen;

$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;

n is an integer from 1 to 3;

and enantiomers, diastereomers, tautomers, solvates, or pharmaceutically acceptable salts thereof.

Still another embodiment of the present invention is directed to analgesic and anti-pyretic uses of compositions comprising a compound of Formula (I) wherein:

$R^1$ and $R^2$ taken together with the atoms to which they are attached form a radical selected from the group consisting of a 5 to 10 membered cycloheteroalkanyl, 5 to 10 membered cycloheteroalkenyl and a 5 to 10 membered heteroaryl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

$R^3$ is hydrogen or $C_{1-6}$alkanyl;

$R^4$ is hydrogen;

n is an integer from 1 to 3;

and enantiomers, diastereomers, tautomers, solvates, or pharmaceutically acceptable salts thereof.

Still yet another embodiment of the present invention is directed to analgesic and anti-pyretic uses of compositions comprising a compound of Formula (I) wherein:

$R^1$ and $R^2$ taken together with the atoms to which they are attached form a radical selected from the group consisting of a 5 to 10 membered cycloheteroalkanyl, 5 to 10 membered cycloheteroalkenyl and a 5 to 10 membered heteroaryl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

$R^3$ is hydrogen or $C_{1-6}$alkanyl;

$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;

n is 1;

and enantiomers, diastereomers, tautomers, solvates, or pharmaceutically acceptable salts thereof.

The present invention is directed to analgesic and anti-pyretic uses of compositions comprising a compound of Formula (II):

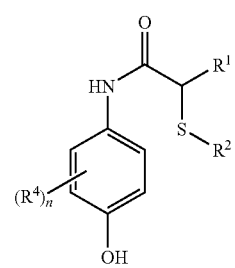

Formula (II)

wherein:

$R^1$ is a substituent independently selected from the group consisting of hydrogen and $C_{1-6}$alkanyl;

$R^2$ is a substituent independently selected from the group consisting of hydrogen, $C_{1-6}$alkanyl and dioxo;

or $R^1$ and $R^2$ taken together with the atoms to which they are attached form a radical selected from the group consisting of a 5 to 10 membered cycloheteroalkanyl, 5 to 10 membered cycloheteroalkenyl and a 5 to 10 membered heteroaryl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;

n is an integer from 1 to 3;

and enantiomers, diastereomers, tautomers, solvates, or pharmaceutically acceptable salts thereof.

Embodiments of the present invention include those wherein for compounds of Formula (II):

a) $R^1$ and $R^2$ taken together with the atoms to which they are attached form a 5 to 10 membered cycloheteroalkanyl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

b) $R^1$ and $R^2$ taken together with the atoms to which they are attached form a 5 to 10 membered cycloheteroalkenyl radical, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

c) $R^1$ and $R^2$ taken together with the atoms to which they are attached form a 5 to 10 membered heteroaryl radical, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

d) $R^1$ and $R^2$ taken together with the atoms to which they are attached form a radical selected from the group consisting of a 5 to 10 membered cycli heteroalkyl and a 5 to 10 membered heteroaryl; additionally, said radical may be further optionally substituted with one to three substituents independently selected from the group consisting of $C_{1-6}$alkanyl and oxo;

e) $R^4$ is hydrogen;

f) n is 1; and g) combinations of a) through f) above.

Thus, exemplary embodiments of the present invention are as described below.

An embodiment of the present invention is directed to analgesic and anti-pyretic uses of compositions comprising a compound of Formula (II) wherein:

$R^1$ and $R^2$ taken together with the atoms to which they are attached form a 5 to 10 membered cycloheteroalkanyl radical, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;

n is an integer from 1 to 3;

and enantiomers, diastereomers, tautomers, solvates, or pharmaceutically acceptable salts thereof.

Another embodiment of the present invention is directed to analgesic and anti-pyretic uses of compositions comprising a compound of Formula (II) wherein:

$R^1$ and $R^2$ taken together with the atoms to which they are attached form a 5 to 10 membered cycli heteroalkenyl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;

n is an integer from 1 to 3;

and enantiomers, diastereomers, tautomers, solvates, or pharmaceutically acceptable salts thereof.

Still another embodiment of the present invention is directed to analgesic and anti-pyretic uses of compositions comprising a compound of Formula (II) wherein:

$R^1$ and $R^2$ taken together with the atoms to which they are attached form a 5 to 10 membered heteroaryl radical, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;

n is an integer from 1 to 3;

and enantiomers, diastereomers, tautomers, solvates, or pharmaceutically acceptable salts thereof.

Still another embodiment of the present invention is directed to analgesic and anti-pyretic uses of compositions comprising a compound of Formula (II) wherein:

$R^1$ and $R^2$ taken together with the atoms to which they are attached form a radical selected from the group consisting of a 5 to 10 membered cycloheteroalkanyl, 5 to 10 membered cycloheteroalkenyl and a 5 to membered heteroaryl; additionally, said radical may be further optionally substituted with one to three substituents independently selected from the group consisting of $C_{1-6}$alkanyl and oxo;

$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;

n is an integer from 1 to 3;

and enantiomers, diastereomers, tautomers, solvates, or pharmaceutically acceptable salts thereof.

Still another embodiment of the present invention is directed to analgesic and anti-pyretic uses of compositions comprising a compound of Formula (II) wherein:

$R^1$ and $R^2$ taken together with the atoms to which they are attached form a radical selected from the group consisting of a 5 to 10 membered cycloheteroalkanyl, 5 to 10 membered cycloheteroalkenyl and a 5 to 10 membered heteroaryl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

$R^4$ is hydrogen;

n is an integer from 1 to 3;

and enantiomers, diastereomers, tautomers, solvates, or pharmaceutically acceptable salts thereof.

Still yet another embodiment of the present invention is directed to analgesic and anti-pyretic uses of compositions comprising a compound of Formula (II) wherein:

$R^1$ and $R^2$ taken together with the atoms to which they are attached form a radical selected from the group consisting of a 5 to 10 membered cycloheteroalkanyl, 5 to 10 membered cycloheteroalkenyl and a 5 to 10 membered heteroaryl, wherein, in addition to the heteroatom N, said radical may optionally contain 1 to 3 additional heteroatoms, independently selected from the group consisting of O, N and S; additionally, said radical may be further optionally substituted with one to three substituents independently selected from the group consisting of $C_{1-6}$alkanyl and oxo;

$R^4$ is a substituent selected from the group consisting of hydrogen, $C_{1-6}$alkanyl, $C_{1-6}$alkanyloxy, fluorinated alkanyl, fluorinated alkanyloxy, halogen, hydroxyl, nitro, amino, $C_{1-6}$alkanylamino; $C_{1-6}$dialkanylamino and cyano;

n is 1;

and enantiomers, diastereomers, tautomers, solvates, or pharmaceutically acceptable salts thereof.

Another embodiment of the present invention is directed to compositions comprising a compound of Formula (I) or Formula (II) wherein said compound is selected from the group consisting of:

Pyridine-2-carboxylic acid (4-hydroxy-phenyl)-amide;
(S)-Pyrrolidine-2-carboxylic acid (4-hydroxy-phenyl)-amide;
N-(4-Hydroxy-phenyl)-2-mercapto-acetamide;
N-(4-Hydroxy-phenyl)-2-methylsulfanyl-acetamide;
N-(4-Hydroxy-phenyl)-2-methanesulfonyl-acetamide;
(R)-Pyrrolidine-2-carboxylic acid (4-hydroxy-phenyl)-amide;
1H-Pyrrole-2-carboxylic acid (4-hydroxy-phenyl)-amide;
1H-Indazole-3-carboxylic acid (4-hydroxy-phenyl)-amide;
5-Methyl-1H-pyrazole-3-carboxylic acid (4-hydroxy-phenyl)-amide; and
3H-Imidazole-4-carboxylic acid (4-hydroxy-phenyl)-amide.

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

A therapeutically effective amount for use of the instant compounds or a pharmaceutical composition thereof comprises a dose range of from about 0.01 mg to about 15,000 mg, in particular from about 1 mg to about 5000 mg or, more particularly from about 500 mg to about 4000 mg of active ingredient per day for an average (70 kg) human.

For oral administration, a pharmaceutical composition is preferably provided in the form of tablets containing, 0.01, 10.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics or anti-pyretics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The compounds of Formulas (I) and (II) are useful in methods for treating a disease or condition in a mammal characterized by pain and/or fever. Such methods comprises administering to a mammal in need of such treatment a therapeutically effective amount of a compound, salt or solvate of Formulas (I) or (II). In particular, the compounds of Formulas (I) and (II) are useful for in methods for control of pain due to headache, earache, dysmenorrhea, arthralgia, myalgia, musculoskeletal pain, arthritis, immunizations, teething, tonsillectomy. They are also used to reduce fever in bacterial or viral infections and as a substitute for aspirin in upper GI disease, aspirin allergy, bleeding disorders, subjects on anticoagulant therapy, and gouty arthritis.

In another embodiment, the compounds of Formulas (I) and (II) are useful in treatment of inflammation.

General Synthetic Methods

Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

The hetero-substituted acaetanilide analogues of formula (I) or formula (II) that comprise this invention are synthesized using the general chemical methods shown in Schemes A through E.

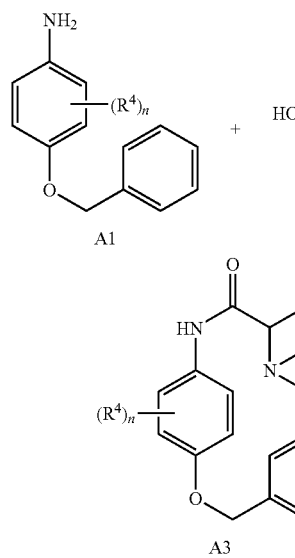

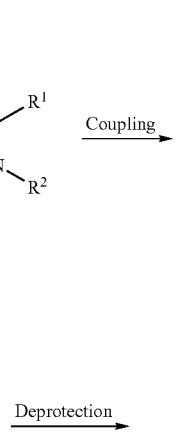

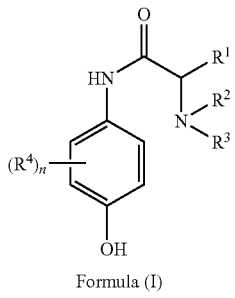

Compounds of Formula (I) are prepared by coupling commercially available anilines A1 with commercially available carboxylic acids A2 in the presence of a coupling reagent such as HBTU, also in the presence of a base such as DIPEA or TEA, also in the presence of a suitable solvent such as DMF which provides protected intermediates A3.

The benzyl protecting group is then removed under hydrogenation conditions under pressures of about 55 psi in the presence of a suitable paladdium catalyst such as 10% palladium on carbon which provides the target compounds of Formula (I).

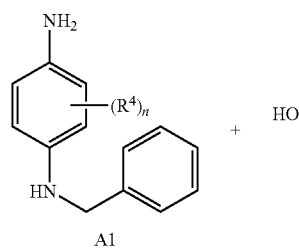

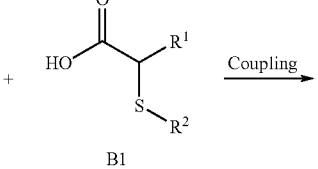

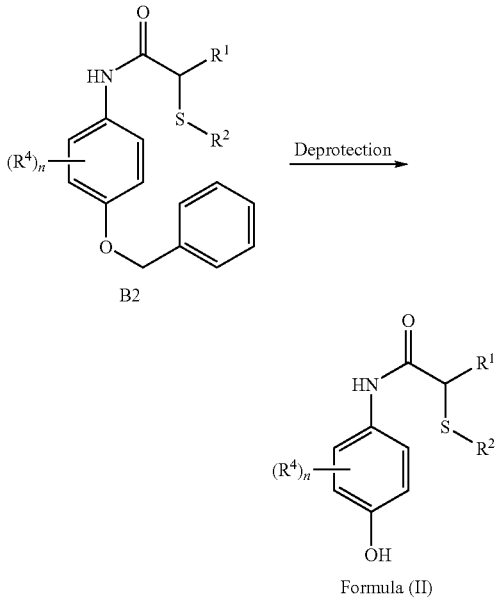

Compounds of Formula (II) are prepared by coupling commercially available anilines A1 with commercially available carboxylic acids B2 in the presence of a coupling reagent such as HBTU, also in the presence of a base such as DIPEA or TEA, also in the presence of a suitable solvent such as DMF which provided protected intermediates B2.

The benzyl protecting group is then removed under hydrogenation conditions under pressures of about 55 psi in the presence of a suitable palladium catalyst such as 10% palladium on carbon which provided the target compounds of Formula (II).

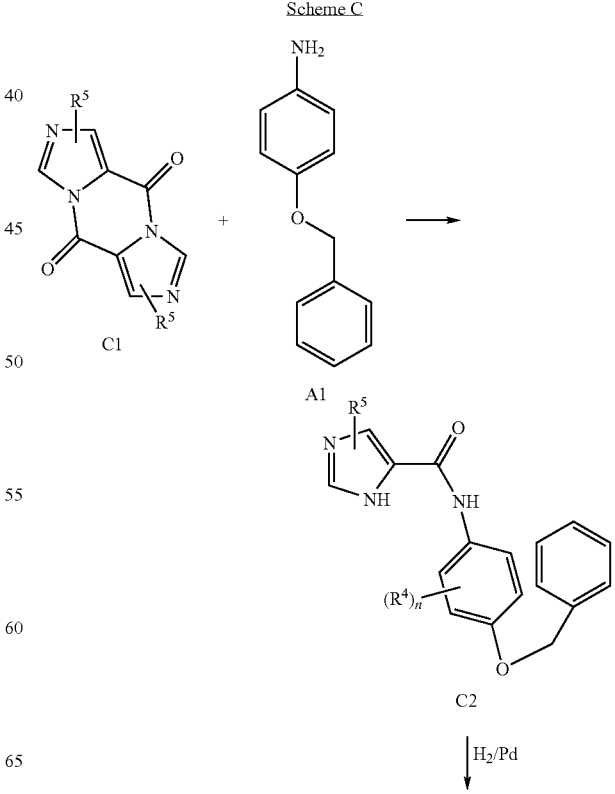

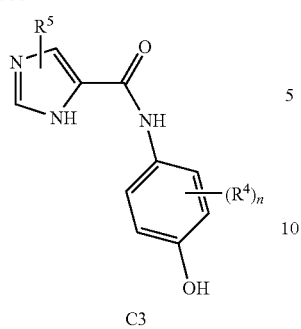

C3

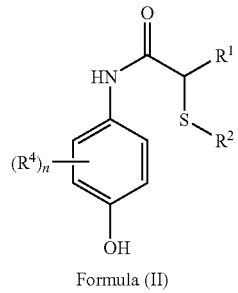

Formula (II)

In the case of certain imidazole compounds, the above described schemes were modified as shown in Scheme C. The carboxylic acid starting material is replaced with the 5-H, 10H-diimidazo[1,5-a, 1',5'-d]pyrazine-5,10-dione C1 which is optionally substituted with $R^5$, wherein $R^5$ is $C_{1-6}$alkyl or oxo, which when reacted directly with anilines A1 upon heating provides the intermediates C2. The protecting group is removed as previously described in schemes A and B to provides compounds C3.

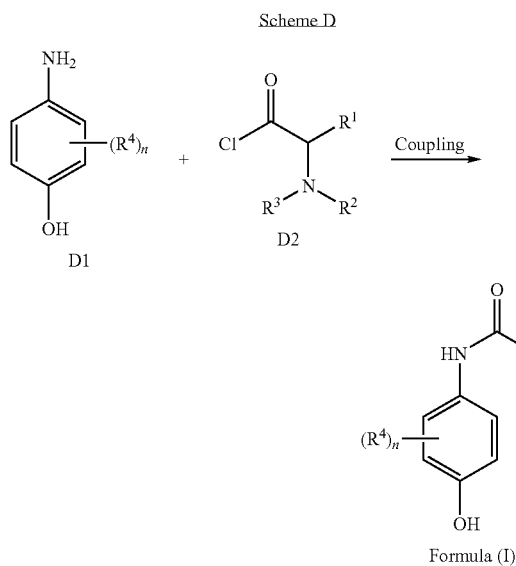

Compounds of Formula (I) may also be prepared by directly coupling a 4-hydroxy aniline D1 with an acid chloride D2 as shown in Scheme D.

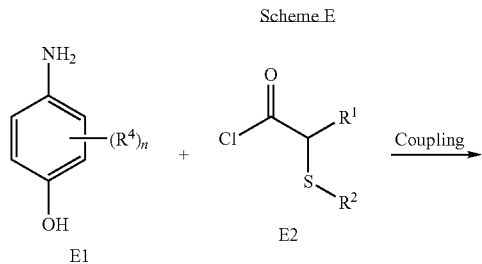

Compounds of Formula (II) may also be prepared by directly coupling a 4-hydroxy aniline E1 with an acid chloride E2 as shown in Scheme E.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halogenhydrocarbon solvents. In those cases where the product is isolated as the acid addition salt the free base may be obtained by techniques known to those skilled in the art. In those cases in which the product is isolated as an acid addition salt, the salt may contain one or more equivalents of the acid.

Representative compounds of the present invention can be synthesized in accordance with the general synthetic methods described above and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

Examples

Example 1

Pyridine-2-carboxylic acid (4-hydroxy-phenyl)-amide

A. Pyridine-2-carboxylic acid (4-benzyloxyphenyl)amide

A solution of pyridine-2-carboxylic acid (2.0 g, 8.48 mmol) in N,N-dimethylformamide (DMF) was treated with O-benzotriazol-1-yl-N,N,N',N'-tetramethyluronium hexafluorophosphate (HBTU) (3.5 g, 9.33 mmol) and N,N-diisopropylethylamine (DIEA) (0.742 mL, 32.7 mmol) and stirred at room temperature for 10 min. 4-Benzyloxyaniline hydrochloride (2.0 g, 8.48 mmol) was added to the solution, and stirring was continued for an additional 30 min. The solution was poured into a saturated aqueous solution of sodium bicarbonate on ice. Mechanically mixing the gummy residue in the bottom of the flask caused it to solidify. The product was collected by filtration, washed with water and dried to give a beige solid, 2.46 g (95%), which was used without further purification in the subsequent reaction. MS m/z 305 (MH$^+$). $^1$H NMR(CDCl$_3$) δ 5.07 (s, 2H), 7.0 (d, 2H), 7.30-7.50 (m, 6H), 7.70 (d, 2H), 7.92 (t, 1H), 8.32 (d, 1H) and 8.58 (d, 1H).

B. Pyridine-2-carboxylic acid (4-hydroxy-phenyl)-amide

A solution of pyridine-2-carboxylic acid (4-benzyloxyphenyl)amide (7.7 g, 25.3 mmol) in 90% ethanol (110 mL) was hydrogenated (60 psi) over 10% palladium on carbon (0.8 g) at 50° C. for 4 hours. The catalyst was removed by filtration, and the solvent was evaporated in vacuo. The residue was purified by flash chromatography on silica gel, using methanol/dichloromethane (DCM), 5/95, as the eluant, to give the product as a beige solid, 2.54 g (47%). MS m/z 215 (MH$^+$). $^1$H NMR (DMSO-d$_6$) δ 6.76 (d, 2H), 7.54 to 7.76 (m, 3H), 8.05 (t, 1H), 8.14 (d, 1H), 8.72 (d, 1H), 9.30 (s, 1H) and 10.41 (s, 1H). Anal. calcd for C$_{12}$H$_{10}$N$_2$O$_2$: C, 67.28; H, 4.71; N, 13.08. Found: C, 66.99; H, 4.56; N, 12.81.

Example 2

N-(4-Hydroxy-phenyl)-2-methanesulfonyl-acetamide

A. N-(4-Benzyloxy-phenyl)-2-methanesulfonyl-acetamide

A solution of 4-benzyloxyaniline hydrochloride (4.0 g, 17.0 mmol), methanesulfonylacetic acid (2.35 g, 17.0 mmol) and HBTU (6.89 g, 18.2 mmol) in DMF (70 mL) was stirred at ambient temperature one minute. DIEA (6.5 mL, 37.2 mmol) was added all at once, and the resultant solution was stirred at ambient temperature. The solution was poured into water, and the product crystallized. The product, 5.4 g (99%), was collected by filtration and was used without any further purification in the subsequent reaction. MS m/z 320 (MH$^+$). $^1$H NMR (DMSO-d$_6$) δ 3.17 (s, 3H), 4.25 (s, 2H), 5.07 (s, 2H), 7.00 (d, 2H), 7.32-7.55 (m, 7H) and 10.32 (s, 1H).

B. N-(4-Hydroxy-phenyl)-2-methanesulfonyl-acetamide

This compound was prepared from N-(4-benzyloxy-phenyl)-2-methanesulfonyl-acetamide, using the same method used to prepare of pyridine-2-carboxylic acid (4-hydroxyphenyl)amide. The product was purified by flash chromatography, on silica gel, eluted with 5 to 10% methanol in DCM, to give the product, 3.45 g (92%) as a colorless solid. MS m/z 230 (MH$^+$). $^1$H NMR (DMSO-d$_6$) δ 3.18 (s, 3H), 4.22 (s, 2H), 6.72 (d, 2H), 7.36 (d, 2H), 9.35 (br s, 1H) and 10.17 (s, 1H). Anal. calcd for C$_9$H$_{11}$N$_4$OS: C, 47.15; H, 4.84; N, 6.11. Found: C, 47.04; H, 4.79; N, 6.04.

Example 3

1H-Pyrrole-2-carboxylic acid (4-hydroxy-phenyl)-amide

A. 1H-Pyrrole-2-carboxylic acid (4-benzyloxy-phenyl)-amide

This compound was prepared from 4-benzyloxyaniline (4.0 g, 17 mmol) and pyrrole-2-carboxylic acid (1.98 g, 17.8 mmol), using the same method used to prepare pyridine-2-carboxylic acid (4-benzyloxyphenyl)amide. The product was purified by flash chromatography, on silica gel, using 5% methanol in DCM as the eluant, to give the product as a colorless solid, 2.6 g (50%). MS m/z 293 (MH$^+$). $^1$H NMR (DMSO-d$_6$) δ 5.04 (s, 2H), 6.13 (m, 1H), 6.95-7.05 (m, 4H), 7.28-7.45 (m, 5H), 7.65 (d, 2H), 9.7 (s, 1H) and 11.65 (s, 1H).

B. 1H-Pyrrole-2-carboxylic acid (4-hydroxy-phenyl)-amide

This compound was prepared from 1H-pyrrole-2-carboxylic acid (4-benzyloxy-phenyl)-amide (2.5 g, 8.55 mmol), using the same method used to prepare of pyridine-2-carboxylic acid (4-hydroxyphenyl)amide. The product was purified by flash chromatography, on silica gel, eluted with 5 to 7.5% methanol in DCM, to give the product as a colorless solid, 1.47 g (85%). MS m/z 203 MH$^+$). $^1$H NMR (DMSO-d$_6$) δ 6.14 (m, 1H), 6.72 (d, 2H), 6.92 (m, 1H), 6.99 (d, 1H), 7.47 (d, 2H), 9.19 (s, 1H). Anal. calcd for C$_{11}$H$_{10}$N$_2$O$_2$: C, 65.34; H, 4.98; N, 13.85. Found: C, 65.15; H, 4.83; N, 13.81.

Example 4

(S)-Pyrrolidine-2-carboxylic acid (4-hydroxy-phenyl)-amide

A. (S)-2-(4-Benzyloxy-phenylcarbamoyl)-pyrrolidine-1-carboxylic acid benzyl ester This compound was prepared from 4-benzyloxyaniline hydrochloride (4.0 g, 17.0 mmol) and (−)-N-carbobenzyloxy-/-proline (4.44 g, 17.8 mmol), using the same method to prepare pyridine-2-carboxylic acid (4-benzyloxyphenyl)amide, to give the product as a colorless solid, 7.51 g (98%), which was used without further purification in the subsequent step. MS m/z 431 (MH$^+$). $^1$H NMR(CDCl$_3$) δ 1.83-2.61 (m, 4H), 3.44-3.65 (m, 2H), 4.40-4.55 (m, 1H), 5.03 (s, 2H), 5.22 (br s, 2H), 6.90 (d, 2H) and 7.20-7.45 (m, 12H).

B. (S)-Pyrrolidine-2-carboxylic acid (4-hydroxy-phenyl)-amide

A suspension of (S)-2-(4-benzyloxy-phenylcarbamoyl)-pyrrolidine-1-carboxylic acid benzyl ester (7.0 g, 16.3 mmol) in ethanol/water (70 mL/7 mL) was hydrogenated over 10% palladium on carbon (0.41 g) at 55 psi of hydrogen, at 50° C., for 5 hours. The mixture was cooled, and the catalyst was removed by filtration. The solvent was evaporated in vacuo. The residue was dissolved in hot ethanol (30 mL) and treated with a saturated solution of hydrogen chloride in ethanol (3 mL). The product crystallized as the hydrochloride salt, 1.27 g (32%), a colorless solid. MS m/z 207 (MH$^+$). $^1$H NMR (DMSO-d$_6$) δ 1.92 (m, 3H), 2.43 (m, 1H), 3.28 (m, 2H), 4.31 (m, 1H), 6.77 (d, 2H), 7.47 (d, 2H), 9.44 (br s, 1H) and 10.75 (s, 1H). Anal. calcd for C$_{11}$H$_{14}$N$_2$O$_2$: C, 54.44; H, 6.23; N, 11.54. Found: C, 54.28; H, 6.06; N, 11.66.

Example 5

(R)-Pyrrolidine-2-carboxylic acid (4-hydroxy-phenyl)-amide

A. (R)-2-(4-Benzyloxy-phenylcarbamoyl)-pyrrolidine-1-carboxylic acid benzyl ester This compound was prepared from 4-benzyloxyaniline hydrochloride (4.0 g, 17.0 mmol) and (+)-N-carbobenzyloxy-d-proline (4.44 g, 17.8 mmol), using the same method to prepare pyridine-2-carboxylic acid (4-benzyloxyphenyl) amide, to give the product as a colorless solid, which was used without further purification in the subsequent step. $^1$H NMR (DMSO-d$_6$) δ 1.80-1.95 (m, 3H), 2.10-2.27 (m, 1H), 3.35-3.55 (m, 2H), 4.33 (m, 1H), 5.0 (m, 4H), 6.95 (d, 2H), 7.12-7.53 (m, 12H) and 9.95 (d, 1H).

B. (R)-Pyrrolidine-2-carboxylic acid (4-hydroxy-phenyl)-amide

This compound was prepared from (R)-2-(4-benzyloxyphenylcarbamoyl)-pyrrolidine-1-carboxylic acid benzyl ester, using the same method used to prepare (S)-pyrrolidine-2-carboxylic acid (4-hydroxy-phenyl)-amide. The free base was dissolved in hot isopropanol (20 mL) and treated with a saturated solution of hydrogen chloride in isopropanol (3 mL). The product crystallized as the hydrochloride salt, 2.43 g (59% for 2 steps). MS m/z 207 (MH$^+$). $^1$H NMR (DMSO-d$_6$) δ 1.93 (m, 3H), 2.39 (m, 1H), 3.26 (m, 2H), 4.35 (t, 1H), 6.76 (d, 2H), 7.43 (d, 2H), 9.43 (br s, 1H) and 10.70 (s, 1H). Anal. calcd for C$_{11}$H$_{14}$N$_2$O$_2$: C, 54.44; H, 6.23; N, 11.54. Found: C, 54.33; H, 6.26; N, 11.57.

Example 6

1H-Indazole-3-carboxylic acid (4-hydroxy-phenyl)-amide

A. 1H-Indazole-3-carboxylic acid (4-benzyloxy-phenyl)-amide

DIEA (9.3 mL, 53.4 mmol) was added to a solution of 4-benzyloxyaniline hydrochloride (4.0 g, 17.0 mmol), indazole-3-carboxylic acid (2.89 g, 17.8 mmol) and HBTU (7.1 g, 18.7 mmol) in DMF (60 mL), and the resulting solution was stirred at ambient temperature for 24 hours. The solution was heated to 70° C. for 4 hours, and then poured into a mixture of saturated aqueous sodium bicarbonate on ice. The product, an off white solid, 6.0 g, was collected by filtration, washed with water and used without further purification in the subsequent reaction. MS m/z 344 (MH$^+$). $^1$H NMR (DMSO-d$_6$) δ 5.11 (s, 2H), 7.02 (d, 2H), 7.26-7.48 (m, 7H), 7.67 (d, 1H), 7.75 (d, 2H), 7.81 (d, 1H), 8.24 (d, 1H) and 10.24 (s, 1H).

B. 1H-Indazole-3-carboxylic acid (4-hydroxy-phenyl)-amide

This compound was prepared from 1H-Indazole-3-carboxylic acid (4-benzyloxy-phenyl)-amide, using the same method used to prepare (S)-pyrrolidine-2-carboxylic acid (4-hydroxy-phenyl)-amide. The product was purified by flash chromatography, on silica gel, eluted with 5 to 10% methanol in DCM, to give the product as an off white solid, 2.6 g (60% for 2 steps). MS m/z 254 (MH$^+$). $^1$H NMR (DMSO-d$_6$) δ 6.74 (d, 2H), 7.26-7.34 (m, 1H), 7.43-7.51 (m, 1H), 7.67-7.73 (m, 3H), 8.24 (d, 1H), 9.25 (s, 1H), 10.10 (s, 1H) and 13.72 (s, 1H). Anal. calcd for C$_{14}$H$_{11}$N$_3$O$_2$: C, 66.40; H, 4.38; N, 16.59. Found: C, 66.15; H, 4.20; N, 16.82.

Example 7

5-Methyl-1H-pyrazole-3-carboxylic acid (4-hydroxy-phenyl)-amide

A. 5-Methyl-1H-pyrazole-3-carboxylic acid (4-benzyloxy-phenyl)-amide

This compound was prepared from 4-benzyloxyaniline hydrochloride (4.0 g, 17.0 mmol) and 5-methylpyrazole-2-carboxylic acid (2.25 g, 17.8 mmol), using the same method used to prepare pyridine-2-carboxylic acid (4-benzyloxyphenyl)amide, to give the product as a solid. The product was used without further purification in the subsequent reaction. MS m/z 308 (MH$^+$). $^1$H NMR(CDCl$_3$+MeOD-d$_4$) δ 2.34 (s, 3H), 5.06 (s, 2H), 6.62 (s, 1H), 6.96 (d, 2H), 7.31 (m, 7H) and 7.58 (d, 1H).

B. 5-Methyl-1H-pyrazole-3-carboxylic acid (4-hydroxy-phenyl)-amide

This compound was prepared from 5-methyl-1H-pyrazole-3-carboxylic acid (4-benzyloxy-phenyl)-amide, using the same method used to prepare pyridine-2-carboxylic acid (4-hydroxyphenyl)amide. The product was purified by flash chromatography, on silica gel, eluted with 5 to 10% methanol in DCM as the eluant, to give the product as an off white solid, 2.75 g (68%). MS m/z 218 (MH$^+$). $^1$H NMR (DMSO-d$_6$) δ 2.28 (s, 3H), 6.47 (s, 1H), 6.71 (d, 2H), 7.55 (d, 2H), 9.19 (s, 1H), 9.67 (s, 1H) and 13.00 (s, 1H). Anal. calcd for C$_{11}$H$_{11}$N$_3$O$_2$; C, 60.08; H, 5.17; N, 19.10. Found: C, 60.00; H, 4.99; N, 19.25.

Example 8

3H-Imidazole-4-carboxylic acid (4-hydroxy-phenyl)-amide

A. 3-H-Imidazole-4-carboxylic acid (4-benzyloxyphenyl)amide

An intimate mixture of 4.25 g (22 mmol) of 5-H, 10H-diimidazo[1,5-a, 1',5'-d]pyrazine-5,10-dione and 9.04 g (45 mmol) of 4-benzyloxyaniline was heated on a steam bath for 30 min. The residue was flash chromatographed with 5% MeOH in CH$_2$Cl$_2$ to give 4.8 g of the title compound (66% yield). MS m/z 294 (MH$^+$). $^1$H NMR(CDCl$_3$) δ 5.07 (s, 2H), 7.0 (d, 2H), 7.30-7.50 (m, 3H), 7.7-7.8 (m, 4H), 9.8 (s 1H), 12.6 (s, 1H).

B. 3-H-Imidazole-4-carboxylic acid (4-hydroxy-phenyl)-amide

A solution of 3-H-imidazole-4-carboxylic acid (4-benzyloxyphenyl)amide. (3.3 g, 11.2 mmol) in glacial acetic acid (70 mL) was hydrogenated (60 psi) over g of 10% palladium on carbon (0.3 g) at 25° C. for 18 hours. The catalyst was removed by filtration, and the solvent was evaporated in vacuo. The residue was stirred with NaHCO$_3$ solution and the solid collected. There was obtained 2.4 g (100% yield) of the title compound as a yellow solid. MS m/z 204 (MH$^+$). $^1$H NMR (DMSO-d$_6$) δ 6.7 (dd, 2H), 7.5 (dd, 2H), 7.7 (s, 1H), 7.8 (s, 1H), 9.1 (s, 1H), 9.6 (s, 1H) and 12.5 (s, 1H).

Example 9

N-(4-Hydroxy-phenyl)-2-mercapto-acetamide

A mixture of 4-aminophenol (4.0 g, 36.7 mmol) and mercaptoacetic acid (2.93 g, 38.5 mmol) under an atmosphere of carbon dioxide was heated to reflux (oil bath temperature ~120° C.) for 4 hours. The mixture was cooled and diluted with 2 N hydrochloric acid (~100 mL). A purple solid, 1.3 g, was collected by filtration and washed with water. The product was purified by flash chromatography, on silica gel, eluted with 5 to 10% methanol in DCM, to give a colorless solid, 1.03 g (15%). MS m/z 184 (MH$^+$). $^1$H NMR (DMSO-d$_6$) δ 2.08 (t, 1H), 3.24 (s, 2H), 6.70 (d, 2H), 7.35 (d, 2H), 9.21 (br s, 1H) and 9.83 (s, 1 H). Anal. calcd for C$_8$H$_9$NO$_2$S: C, 52.44; H, 4.95; N, 7.64. Found: C, 52.57; H, 4.95; N, 7.40.

Biological Examples

Example 1

Mouse Abdominal Irritant Test (MAIT)

Male CD1 mice (weighing from 18-24 g) are used to determine the antinociceptive effects associated with the compositions of the invention. The mice are all dosed orally with the compounds specified, dissolved in distilled water or suspended in 0.5% Methocel™ (hydroxypropyl methylcellulose) in water. The dosing volume is 10 mL/kg.

The procedure used in detecting and comparing the analgesic activity of different classes of analgesic drugs for which there is a good correlation with human efficacy is the prevention of acetylcholine-induced abdominal constriction in mice (H. Collier et al., Br. J. Pharmacol., 32, 295 (1968)).

Mice, intubated with various doses of the compound or vehicle such as distilled water, or distilled water 0.5% Methocel™ (hydroxypropyl methylcellulose) in water, are injected intraperitoneally with a challenge dose of acetylcholine bromide. The acetylcholine is completely dissolved in distilled water at a concentration of 5.5 mg/kg and injected at the rate of 0.20 mL/20 g. For scoring purposes, an "abdominal constriction" is defined as a contraction of the abdominal musculature accompanied by arching of the back and extension of the limbs. The mice are observed for 10 minutes for the presence or absence of the abdominal constriction response beginning immediately after receiving the acetylcholine dose, administered at a certain time after the oral administration of the test drug or vehicle. Each mouse is used only once.

The percent of inhibition of this response is calculated as follows:

%Inhibition=100×(Number of Nonresponders)/(Number of Animals in Group)

TABLE 2

Antinociceptive Effect in Mouse Abdominal Irritant Test

| Compound | Effect @ 300 mg/kg |
|---|---|
| Pyridine-2-carboxylic acid (4-hydroxy-phenyl)-amide | 60.0 |
| (S)-Pyrrolidine-2-carboxylic acid (4-hydroxy-phenyl)-amide | 40.0 |
| N-(4-Hydroxy-phenyl)-2-methylsulfanyl-acetamide | 45.0 |
| N-(4-Hydroxy-phenyl)-2-methanesulfonyl-acetamide | 40.0 |
| (R)-Pyrrolidine-2-carboxylic acid (4-hydroxy-phenyl)-amide | 20.0 |
| 1H-Pyrrole-2-carboxylic acid (4-hydroxy-phenyl)-amide | 86.7 |
| 1H-Indazole-3-carboxylic acid (4-hydroxy-phenyl)-amide | 20.0 |
| 5-Methyl-1H-pyrazole-3-carboxylic acid (4-hydroxy-phenyl)-amide | 73.3 |
| N-(4-Hydroxy-phenyl)-2-mercapto-acetamide | 40.0 |

Example 2

Antipyretic Evaluation of Compounds

Groups of 10 male rats are weighed, color-coded, rectal temperatures taken (24 hours±15 minutes prior to dose administration) and recorded. Food is removed but water remains available ad libitum. Each rat is injected subcutaneously into the central dorsal region with 5 ml of a 15% yeast suspension. Twenty-three hours (±15 minutes) after yeast injection, body weights and rectal temperatures are taken and recorded. Twenty-four hours (±15 minutes) after yeast injection, the vehicle and test articles are administered orally. Temperatures are taken and recorded one hour (±5 minutes) following test article or vehicle administration.

The mean rectal temperatures for the test article and vehicle control groups are calculated at 23 and 25 hours (±15 minutes) and subjected to an ANOVA followed by a Tukey HSD Multiple Comparison Test (p≦0.05)–Systat, version 9.0.

As represented in Table 3, the oral administration of compound 1, at 600 mg/kg produces a statistically significant (p≦1.05) decrease in body temperature in rats relative to the vehicle-treated group.

TABLE 3

Antipyretic Effect in Rats

| Compound | Antipyresis deg C. @ 600 mpk |
|---|---|
| Pyridine-2-carboxylic acid (4-hydroxy-phenyl)-amide | −2.17 |

The invention claimed is:

1. A method of controlling pain or fever in a subject in need thereof comprising administering to the subject a therapeutically effective amount of a compound of Formula (I):

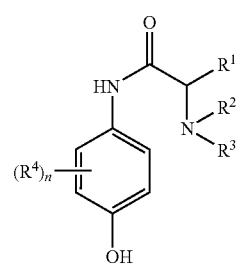

(I)

wherein $R^3$ is hydrogen and $R^1$ and $R^2$ taken together form an optionally substituted selected from the group consisting of pyarazole, and imidazole;
$R^4$ is a hydrogen;
n is an integer from 1 to 3;
and enantiomers, diastereomers, tautomers, or pharmaceutically acceptable salts thereof.

2. The method of controlling pain or fever of claim 1, wherein $R^1$ and $R^2$ taken together form an optionally substituted imidazole and enantiomers, diastereomers, tautomers, or pharmaceutically acceptable salts thereof.

3. A method of controlling pain or fever in a subject in need thereof comprising administering to the subject a therapeutically effective amount of a compound selected from the group consisting of:
   5-Methyl-1H-pyrazole-3-carboxylic acid (4-hydroxy-phenyl)-amide; and
   3H-Imidazole-4-carboxylic acid (4-hydroxy-phenyl)-amide;
   and enantiomers, diastereomers, tautomers, or pharmaceutically acceptable salts thereof.

4. The method of controlling pain or fever of claim 3, wherein the compound is 5-Methyl-1H-pyrazole-3-carboxylic acid (4-hydroxy-phenyl)-amide and enantiomers, diastereomers, tautomers, or pharmaceutically acceptable salts thereof.

* * * * *